(12) United States Patent
Boutinon

(10) Patent No.: US 10,499,807 B2
(45) Date of Patent: Dec. 10, 2019

(54) VISION-COMPENSATING DEVICE, METHOD FOR CONTROLLING A VISION-COMPENSATING DEVICE AND BINOCULAR OPTOMETRY DEVICE

(71) Applicant: ESSILOR INTERNATIONAL (COMPAGNIE GENERALE D'OPTIQUE), Charenton-le-Pont (FR)

(72) Inventor: Stephane Boutinon, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 0 days.

(21) Appl. No.: 15/743,294

(22) PCT Filed: Jul. 15, 2016

(86) PCT No.: PCT/FR2016/051827
§ 371 (c)(1),
(2) Date: Jan. 10, 2018

(87) PCT Pub. No.: WO2017/013343
PCT Pub. Date: Jan. 26, 2017

(65) Prior Publication Data
US 2018/0199808 A1 Jul. 19, 2018

(30) Foreign Application Priority Data
Jul. 17, 2015 (FR) ...................................... 15 56795

(51) Int. Cl.
*A61B 3/028* (2006.01)
*A61B 3/00* (2006.01)
*A61B 3/036* (2006.01)

(52) U.S. Cl.
CPC .......... *A61B 3/0285* (2013.01); *A61B 3/0033* (2013.01); *A61B 3/028* (2013.01); *A61B 3/036* (2013.01)

(58) Field of Classification Search
CPC ..... A61B 3/0285; A61B 3/036; A61B 3/0033; A61B 3/028; A61B 3/04; A61B 3/0025
(Continued)

(56) References Cited

U.S. PATENT DOCUMENTS

| 3,927,933 A | 12/1975 | Humphrey |
| 4,113,363 A | 9/1978 | Humphrey |

(Continued)

FOREIGN PATENT DOCUMENTS

| EP | 2 034 338 A1 | 3/2009 |
| WO | 2007/026368 A2 | 3/2007 |
| WO | 2015/107303 A1 | 7/2015 |

OTHER PUBLICATIONS

International Search Report, dated Oct. 20, 2016, from corresponding PCT/FR2016/051827 application.

*Primary Examiner* — Tuyen Tra
(74) *Attorney, Agent, or Firm* — Young & Thompson

(57) ABSTRACT

A vision-compensating device allowing observation along an optical axis of observation with an optical correction of variable power includes a lens having, along the optical axis, a spherical power that is variable as a function of a first control, and an optical assembly generating, along the optical axis, a cylindrical correction that is variable as a function of at least one second control applied to the optical assembly. The vision-compensating device also includes a module for receiving at least one setpoint for the optical correction and a module for determining the first control and the second control depending on the setpoint by way of a mode taking into account the distance separating the lens
(Continued)

and the optical assembly. A method for controlling a vision-compensating device and a binocular optometry device are also proposed.

12 Claims, 2 Drawing Sheets

(58) Field of Classification Search
USPC ....... 351/200, 222, 118, 227, 228, 233, 229, 351/235, 246
See application file for complete search history.

(56) References Cited

U.S. PATENT DOCUMENTS

| | | | |
|---|---|---|---|
| 10,278,573 B2* | 5/2019 | Boutinon | A61B 3/0025 |
| 2004/0032568 A1 | 2/2004 | Fukuma et al. | |
| 2013/0088686 A1* | 4/2013 | Graziano | A61B 3/145 |
| | | | 351/206 |
| 2016/0331226 A1 | 11/2016 | Nauche et al. | |

* cited by examiner

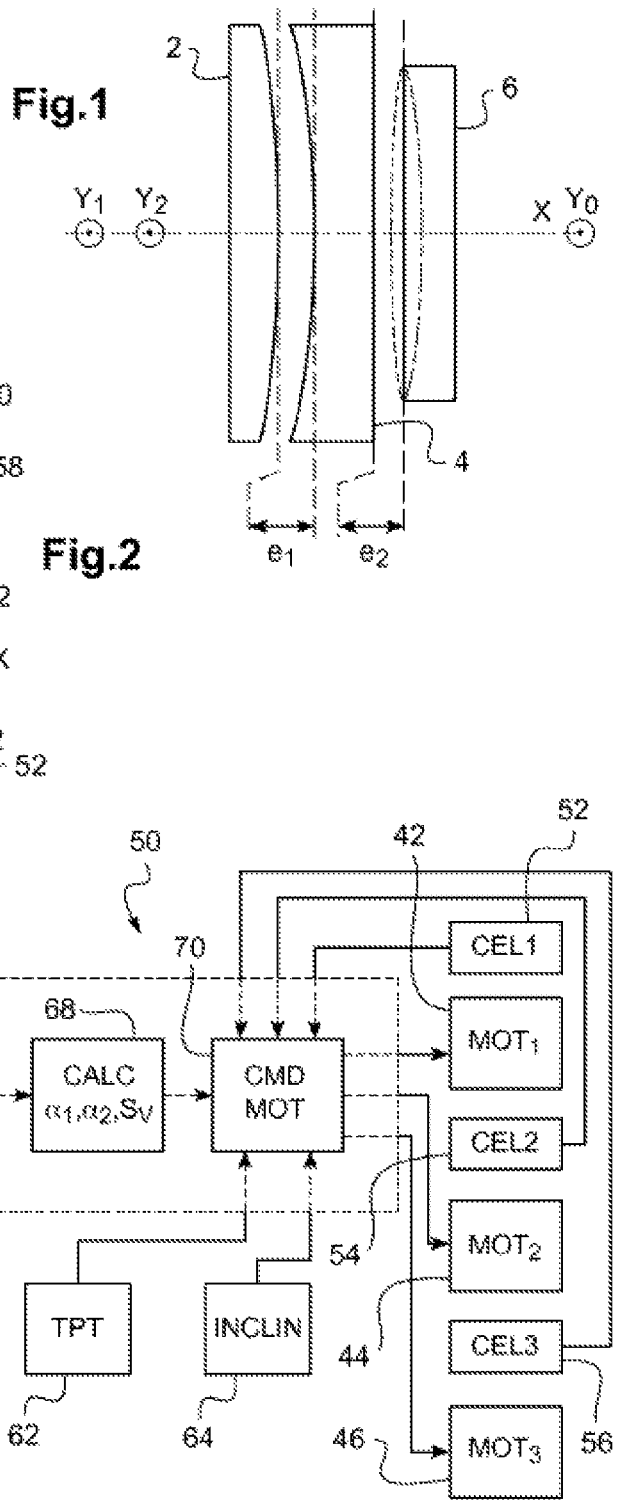

VISION-COMPENSATING DEVICE, METHOD FOR CONTROLLING A VISION-COMPENSATING DEVICE AND BINOCULAR OPTOMETRY DEVICE

TECHNICAL FIELD OF THE INVENTION

The present invention relates to pieces of optometry equipment that are in particular intended for subjective eye tests.

It more particularly relates to a visual compensation device, to a method for controlling a visual compensation device and to an optometric binocular device.

TECHNOLOGICAL BACKGROUND

In the context of subjective eye tests, a visual compensation device is generally used to allow observation along an optical axis of observation with an optical correction of variable power.

For example, such a device is for example known from document US 2004/032 568; this device comprises a lens having, along the optical axis, a variable spherical power that depends on a first setting, and an optical assembly generating, along the optical axis, a variable cylindrical correction that depends on at least one second setting applied to said optical assembly.

In such a system it is for example proposed to display on a screen the optical correction values obtained by applying current settings, thereby allowing the practitioner to modify the settings to obtain other optical correction values.

This solution is however impractical since it obliges the practitioner to find by trial and error the visual correction values that he desires to test during the subjective eye test.

SUBJECT OF THE INVENTION

In this context, the present invention provides a visual compensation device allowing observation along an optical axis of observation with an optical correction of variable power, comprising a lens having, along the optical axis, a variable spherical power that depends on a first setting, and an optical assembly generating, along the optical axis, a variable cylindrical correction that depends on at least one second setting applied to said optical assembly, characterized by a module for receiving at least one setpoint for said optical correction, and by a module for determining the first setting and the second setting depending on said setpoint by means of a model taking into account the distance separating said lens and said optical assembly.

Because the aforementioned distance, i.e. the spacing between the lens and the optical assembly, is taken into account, coupling effects generated by this spacing are taken into account and, after the first setting and the second setting have been applied to the lens and to the optical system, respectively, a correction that corresponds precisely to the setpoint (i.e. to the correction desired by the practitioner) is obtained.

The module for determining the first setting and the second setting may furthermore comprise a module for determining an approximate first setting value and an approximate second setting value depending on said setpoint, a module for evaluating, on the basis of said model, at least one correction value obtained by applying the approximate first setting value to the lens and the approximate second setting value to the optical assembly, and a module for determining a corrected first setting value and a corrected second setting value on the basis of a comparison between the setpoint and the evaluated correction value.

The module for determining the first setting and the second setting may then use the first corrected setting value and the second corrected setting value respectively by way of first setting and second setting.

Thus, in real-time, setting values are obtained that allow the desired setpoint values to be obtained.

According to another envisionable embodiment, the module for determining the first setting and the second setting may be designed to read the first setting (and optionally the second setting) from a look up table constructed on the basis of said model.

In certain embodiments, the optical assembly may comprise a second lens and a third lens; the model may in this case also take into account the distance separating the second lens and the third lens.

The invention also provides a method for controlling a visual compensation device allowing observation along an optical axis of observation with an optical correction of variable power and comprising a lens and an optical assembly, characterized in that it comprises the following steps:
  receiving at least one setpoint for said optical correction;
  determining a first setting and a second setting depending on said setpoint by means of a model taking into account the distance separating said lens and said optical assembly;
  modifying the spherical power of the lens along the optical axis depending on the first setting; and
  modifying a cylindrical correction generated along the optical axis by the optical assembly depending on the second setting.

The step of determining a first setting and a second setting may comprise the following substeps:
  determining an approximate first setting value and an approximate second setting value depending on said setpoint;
  evaluating, on the basis of said model, at least one correction value obtained by applying the approximate first setting value to the lens and the approximate second setting value to the optical assembly;
  determining a corrected first setting value and a corrected second setting value on the basis of a comparison between the setpoint and the evaluated correction value.

The control method may then optionally comprise the following substeps:
  evaluating, on the basis of said model, at least one new correction value obtained by applying the corrected first setting value to the lens and the corrected second setting value to the optical assembly;
  determining a new corrected first setting value and a new corrected second setting value on the basis of a comparison between the setpoint and the evaluated new correction value.

In this case, the substeps of evaluating at least one new correction value and determining a new corrected first setting value and a new corrected second setting value may be reiterated provided that the distance between the setpoint and the evaluated new correction value is larger than a preset threshold.

According to the aforementioned variant, the step of determining a first setting and a second setting may comprise a sub-step of reading the first setting (and optionally the second setting) from a look up table constructed on the basis of said model.

The invention also provides an optometric binocular device comprising two optical devices, which are for example mounted on a common holder, wherein one of the two optical devices (or even each of the two optical devices) is a visual compensation device as presented above.

DETAILED DESCRIPTION OF AN EXEMPLARY EMBODIMENT

The description which follows with reference to the appended drawings, which are given by way of nonlimiting examples, will make it easy to understand what the invention consists of and how it can be achieved.

In the appended drawings:

FIG. 1 schematically shows the optical elements used in one example implementation of the invention;

FIG. 2 shows a cross-sectional view of an exemplary visual compensation device according to the teachings of the invention;

Figure 6:
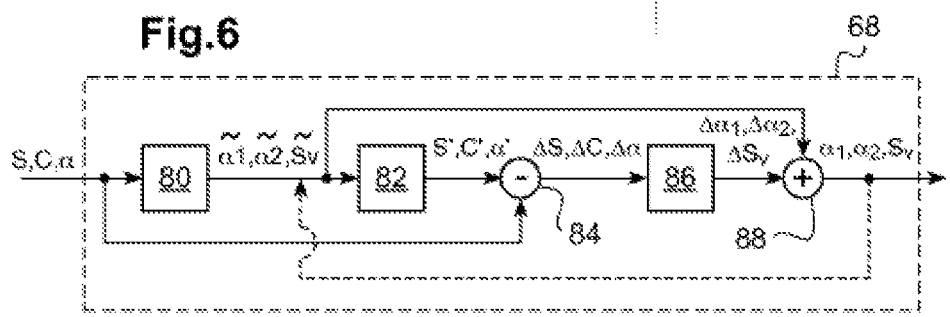

FIG. 5 schematically shows an element for controlling the visual compensation device in FIG. 2;

FIG. 6 shows an example of a possible way in which a module allowing the control element of FIG. 5 to be computed may be constructed.

FIG. 1 schematically shows the main optical elements of an exemplary visual compensation device according to the teachings of the invention.

These optical elements comprise a convex planar-cylindrical lens 2, of cylindrical power $C_1$ (here equal to $C_0$), a concave planar-cylindrical lens 4, of cylindrical power $C_2$ (here negative and equal to $-C_0$), and a lens 6 of variable spherical power $S_V$.

The absolute value (or modulus), here $C_0$, of the cylindrical power (here $-C_0$) of the concave planar-cylindrical lens 4 is therefore equal to the absolute value ($C_0$) (or modulus) of the cylindrical power ($C_0$) of the convex planar-cylindrical lens 2.

These three lenses 2, 4, 6 are placed on the same optical axis X. Precisely, each of the three lenses 2, 4, 6 has a generally cylindrical exterior shape centered on the optical axis X. In the example described here, the lenses 2, 4, 6 have the following diameters (quantifying their bulk), respectively: 25 mm, 25 mm, 20 mm.

It will be noted that it is preferable to use this visual compensation device 10 with the eye of the patient located on the side of the variable spherical power lens 6 so that the cylindrical power lenses 2, 4, which are larger in diameter, do not limit the field of view defined by the variable spherical power lens 6, which itself is perceived as large due to its proximity to the eye of the patient.

Each of the three lenses 2, 4, 6 comprises a first planar face, perpendicular to the optical axis X, and a second face, opposite the first face and optically active:

the optically active face of the lens 2 is cylindrically convex in shape (the axis $Y_1$ of the cylinder defining this face lying perpendicular to the optical axis X);

the optically active face of the lens 4 is cylindrically concave in shape (the axis $Y_2$ of the cylinder defining this face lying perpendicular to the optical axis X); and the optically active face of the lens 6 of variable spherical power $S_V$ is deformable and may thus be given a convex spherical shape (as illustrated by the line of equal length dashes in FIG. 1), a planar shape (as illustrated by the solid line) or a concave spherical shape (as illustrated by the line of unequal length dashes).

The lens 6 of variable spherical power $S_V$ is for example a lens of the type described in document EP 2 034 338. Such a lens comprises a cavity closed by a transparent deformable membrane and a planar movable transparent wall; the cavity contains a transparent liquid of constant volume that is constrained, to a greater or lesser degree, by the movable face, in order to deform the membrane that is thus either a spherical concave surface, or a planar surface, or a spherical convex surface. In the lens used, a transformation of motion achieved with a nut/bolt system makes it possible to ensure transformation of rotary and linear motion. Thus, rotating a ring mounted on a casing 26 translates a part of the lens 6, thereby causing the aforementioned deformation of the transparent membrane, as explained for example in the aforementioned document EP 2 034 338. It is thus possible to vary the spherical power $S_V$ continuously via mechanical action on the lens 6. In the example described here, the lens 6 has a variable focal length of between −40 mm and 40 mm, i.e. a variable spherical power $S_V$ of between −25 D and 25 D (D being the diopter, the unit for measuring vergence, inverse to the focal length expressed in meters).

Moreover, the planar-cylindrical lenses 2, 4 have respectively as already indicated a cylindrical power of $-C_0$ and $C_0$, here with $C_0=5$ D.

As explained in greater detail below, the concave planar-cylindrical lens 4 and the convex planar-cylindrical lens 2 are rotatably mounted about the axis X (rotation centered on the axis X).

The axis $Y_1$ of the convex cylinder formed on the optically active face of the convex planar-cylindrical lens 2 may thus make a variable angle $\alpha_1$ with a reference axis $Y_0$ (which is fixed and perpendicular to the optical axis X).

Likewise, the axis $Y_2$ of the concave cylinder formed on the optically active face of the concave planar-cylindrical lens 4 may make a variable angle $\alpha_2$ with the reference axis $Y_0$.

The convex planar-cylindrical lens 2 and the concave planar-cylindrical lens 4 are spaced apart by a distance $e_1$ along the optical axis; the concave planar-cylindrical lens 4 and the lens 6 of variable spherical power $S_V$ are spaced apart by a distance $e_2$ along the optical axis. In the embodiment described below with reference to FIG. 2, $e_1$ is for example (about) 1 mm (generally, $e_1$ may be comprised between 0.5 mm and 2 mm) and $e_2$ is for example (about) 5 mm (generally, $e_2$ may be comprised between 2 mm and 10 mm).

In order to explain the optical behavior of the system that has just been described in a simple way, the formulae for the spherical power S, the cylindrical power C and the angle of astigmatism $\alpha$ of the system formed from the three optical elements 2, 4, 6 will be given below, these formulae being obtained by calculating the vergence on the various meridians in a model in which the coupling effect caused by the spacings $e_1$, $e_2$ between the various lenses is neglected:

$$\tan 2\alpha = \frac{\sin 2\alpha_2 - \sin 2\alpha_1}{\cos 2\alpha_2 - \cos 2\alpha_1} = -\frac{\cos(\alpha_1 + \alpha_2)}{\sin(\alpha_1 + \alpha_2)} \quad \text{(formula 1)}$$

$$C = C_0(\cos 2(\alpha - \alpha_2) - \cos 2(\alpha - \alpha_1)) \quad \text{(formula 2)}$$

$$S = S_V - \frac{C}{2}. \quad \text{(formula 3)}$$

It will be noted that the term (−C/2) in formula 3 corresponds to spherical power generated by the resultant of the 2 lenses providing cylindrical power.

By setting the rotational position of the convex planar-cylindrical lens 2 and the rotational position of the concave planar-cylindrical lens 4 independently of each other, as described below, it is possible to vary, independently, each of the angles $\alpha_1$ and $\alpha_2$ from 0° to 360° and thus obtain a cylindrical power C adjustable between −2.$C_0$ and 2.$C_0$ (i.e. here between −10 D and 10 D) for any angle of astigmatism, adjustable between 0° and 360°, obtained by controlling the two lenses simultaneously. As formula 3 indicates, the spherical power resulting from the resultant of the orientation of the 2 cylindrical lenses is compensated for using the spherical lens of variable power.

Moreover, by varying the spherical power $S_V$ of the spherical lens 6, it is possible to adjust the spherical power S of the system formed from the three lenses 2, 4, 6.

According to one envisionable variant, the lenses providing a set cylindrical power could have the same (positive or negative) cylindrical power $C_0$: it could be a question of two, optionally identical, convex planar-cylindrical lenses or, as an alternative, of two, optionally identical, concave planar-cylindrical lenses.

Specifically, in this case, the spherical power S, the cylindrical power C and the angle of astigmatism α of the system formed from these two lenses and from a lens providing variable spherical power are given by the following formulae:

$$\tan 2\alpha = \frac{\sin 2\alpha_2 + \sin 2\alpha_1}{\cos 2\alpha_2 + \cos 2\alpha_1} \quad \text{(formula 4)}$$

$$C = C_0(\cos 2(\alpha - \alpha_2) + \cos 2(\alpha - \alpha_1)) \quad \text{(formula 5)}$$

$$S = S_V + C_0 - \frac{C}{2}. \quad \text{(formula 6)}$$

The term $C_0$−C/2 corresponds to the spherical power induced by the combination of the two lenses providing cylindrical power.

It is therefore also possible in this case to adjust the spherical power S, the cylindrical power C and the angle of astigmatism α, in particular so that the hcylindrical power C is zero, by rotating the lenses providing cylindrical power (independently of each other) and by varying the spherical power of the lens providing variable spherical power.

An example visual compensation device 10 that uses the optical elements that have just been described is shown in FIG. 2.

Sometimes in the following description, in order to clarify the explanation, terms such as "upper" or "lower" will be used, which define an orientation in FIGS. 2, 3 and 4. It will be understood that this orientation is not necessarily applicable to the use that will possibly be made of the device described, in which use the only reference direction is the optical axis X.

The visual compensation device 10 comprises a casing 12 formed from a first portion 14, a second portion 16 and a third portion 18, which are placed in succession along the optical axis X and assembled pairwise in planes perpendicular to the optical axis X.

A first toothed wheel 22 is mounted so as to be able to rotate with a rotary movement centered on the optical axis X in the first portion 14 of the casing 12 and bears, at its center, in an aperture provided for this purpose, the convex planar-cylindrical lens 2. The first toothed wheel 22 and the convex planar-cylindrical lens 2 are coaxial; in other words, in cross section in a plane perpendicular to the optical axis X, the exterior circumference of the first toothed wheel 22 and the circumference of the convex planar-cylindrical lens 2 form concentric circles centered on the optical axis X.

Likewise, a second toothed wheel 24 is mounted so as to be able to rotate with a rotary movement centered on the optical axis X in the second portion 16 of the casing 12 and bears, at its center, in an aperture provided for this purpose, the concave planar-cylindrical lens 4. The second toothed wheel 24 and the concave planar-cylindrical lens 4 are coaxial; in other words, in cross section in a plane perpendicular to the optical axis X, the exterior circumference of the second toothed wheel 24 and the circumference of the concave planar-cylindrical lens 4 form concentric circles centered on the optical axis X.

A third toothed wheel 27 is mounted so as to be able to rotate with a rotary movement centered on the optical axis X in the third portion 18 of the casing 12. The third toothed wheel 27 is securely fastened to the ring provided on the circumference of the casing 26 that bears the lens 6 of variable spherical power and allowing the spherical power $S_V$ to be controlled. The casing 26 of the lens 6 of variable spherical power is mounted in the third portion 18 of the casing 12.

Figure 3:
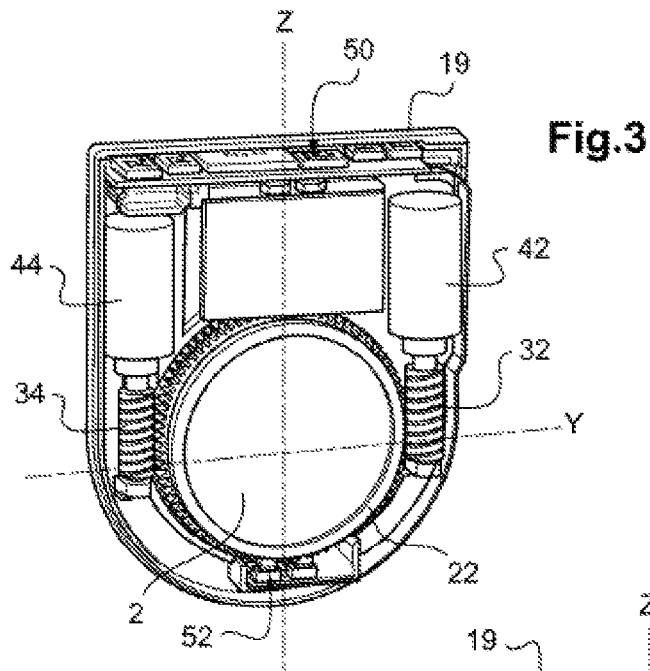
FIG. 3 shows a cutaway view of the compensation device in FIG. 2, from the side of the cylindrical lenses.

As may be clearly seen in FIG. 3, the first toothed wheel 22 is rotated (about the optical axis X) by means of a first motor 42 a drive axis of which bears a first worm screw 32 that engages with the first toothed wheel 22. The first motor 42 is for example mounted in the first portion 14 of the casing 12.

The current position of the first toothed wheel 22 is monitored by a first optical cell 52.

Likewise, the second toothed wheel 24 is rotated about the optical axis X by means of a second motor 44 a drive axis of which bears a second worm screw 34 that engages with the second toothed wheel 24. The second motor 44 is for example mounted in the second portion 16 of the casing 12.

The current position of the second toothed wheel 24 is monitored by a second optical cell 54.

Figure 4:
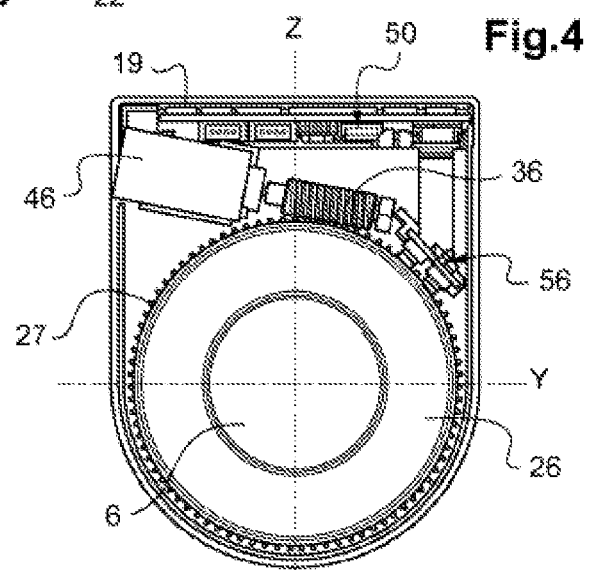
FIG. 4 shows a cutaway view of the compensation device in FIG. 2, from the side of the variable spherical lens.

As shown in FIG. 4, the third toothed wheel 27 is for its part rotated (about the optical axis X) by means of a third motor 46 that has a drive axis on which a third worm screw 36 that engages with the third toothed wheel 27 is mounted. The third motor 46 is for example mounted in the third portion 18 of the casing 12.

The current position of the third toothed wheel 27 is monitored by a third optical cell 56.

Each optical cell 52, 54, 56 is for example formed from a pair of elements comprising at least one optical sensor; the other element of the pair is for example an optical emitter (or, as a variant, a reflective element, in which case an optical emitter is associated with the optical sensor).

The first, second and third motors 42, 44, 46 are for example stepper motors having a resolution of 20 steps/turn, here set in 8ths of a step (referred to as micro-steps below). As a variant, these motors could be set in 16ths of a step. As a variant, it could be a question of DC motors with coders.

The internal volume of the casing 12 (and moreover the internal volume of each of the first, second and third portions 14, 16, 18 in the same way) may be subdivided into a space for receiving the motors 42, 44, 46 (upper region of the casing 12 in FIGS. 2, 3 and 4) and a space for receiving the optical elements 2, 4, 6 (lower region of the casing 12 in FIGS. 2, 3 and 4).

The space for receiving the motors 42, 44, 46 has an essentially parallelepipedal shape open (toward the bottom in the figures) in the direction of the space for receiving the optical elements 2, 4, 6 and closed at the opposite end (toward the top in the figures) by an upper face 19 of the casing 12 (the upper face 19 of the casing 12 being formed by the assembled upper faces of the first, second and third portions 14, 16, 18 of the casing 12, respectively).

The arrangement of the motors 42, 44 and 46 is such as to advantageously make it possible to use a circular geometry over 180°, said circular geometry being centered on the optical axis as close as possible to the useful radius of the lenses.

The space for receiving the optical elements 2, 4, 6 has, in contrast to the space for receiving the motors, a cylindrical shape (bounded by the walls of the casing 12) that matches that of the third toothed wheel 27 over half the circumference of the latter.

In other words, the casing 12 (and therefore each of the first, second and third portions 14, 16, 18 of the casing 12) has, in the space for receiving the optical elements 2, 4, 6, a cylindrical shape with a diameter (perpendicular to the optical axis X) that is about the same as, and slightly larger than, that of the third toothed wheel 27.

The respective diameters of the toothed wheels 22, 24, 27 are chosen so as to promote preservation of the field despite the thickness of the optical system.

The first motor 42 and the first worm screw 32 extend in the casing 12 in a direction Z perpendicular to the upper face of the casing 12 (and therefore especially perpendicular to the optical axis X) in such a way that the first motor 42 is housed in the space for receiving the motors whereas the first worm screw 32 lies in the space for receiving the optical elements.

As for the second motor 44 and the second worm screw 34, they extend in the casing 12 in the same direction, but opposite the first motor 42 and the first worm screw 34 relative to the cylindrical power lenses 2, 4. The second motor 44 is housed in the space for receiving the motors whereas the second worm screw 34 lies in the space for receiving the optical elements.

Thus, it will be noted that the first worm screw 32 and the second worm screw 34 are located on either side of the assembly formed by the first toothed wheel 22 and the second toothed wheel 24, and that the lateral bulk (along an axis Y perpendicular to the aforementioned axes X and Z) of these various parts (first worm screw 32, second worm screw 34, first or second toothed wheel 22, 24) is smaller than the diameter of the third toothed wheel 27 so that the first and second worm screws 32, 34 are contained in the space for receiving the optical elements without extra room being required to receive them.

Moreover, the first and second motors 42, 44 each have a bulk along the optical axis X larger than that of each of the first and second toothed wheels 22, 24, and even larger than that of each of the first and second portions 14, 16 of the casing 12. However, because these first and second motors 42, 44 are placed as indicated above on each side of the casing 12 (relative to the axis Z), they may each occupy a space that extends, along the optical axis X, in line with the first portion 14 and the second portion 16 of the casing 12.

For example, each of the first and second motors 42, 44 has a lateral bulk (outside diameter of the motor) comprised between 6 and 12, for example 10 mm, whereas the first and second toothed wheels 22, 24 each have a thickness (bulk along the axis X) comprised between 1 and 4, for example 2.5 mm.

The third motor 46 and the third worm screw 36 are in contrast located in the space for receiving the motors, in the region that extends along the axis X in line with the third portion 18 of the casing 12. Thus, the third worm screw 36 engages with the third toothed wheel 27 in an upper portion of the latter, thereby making it possible for the casing 12 to follow closely the shape of the casing 12 in the lower portion of the third toothed wheel 27, as indicated above.

In the example described, as shown in FIG. 4, the axis of the third motor 46 and the third worm screw 36 is slightly inclined relative to the upper face of the casing 12 (specifically relative to the aforementioned axis Y).

Provision is for example made for the thickness of the third toothed wheel 27 to be comprised between 0.3 mm and 2 mm.

This arrangement of the various elements allows a relatively thin casing to be obtained, typically having a thickness comprised between 15 and 20 mm.

The casing 12 also comprises, for example in the upper region of the space for receiving the motors, a control element 50, here formed of a plurality of integrated circuits borne by a common printed circuit board.

Moreover a device for storing electrical power, here a battery 58 (though, as a variant, it could be a supercapacitor), is provided in order to make the apparatus standalone. Provision is for example also made for contactless elements for recharging the power storing device 58. The battery 58 especially allows the motors 42, 44, 46 and the control element 50 to be supplied with electrical power.

The main elements of such a control element 50, and their connections to the aforementioned motors 42, 44, 46 and to the aforementioned optical cells 52, 54, 56, are schematically shown in FIG. 5.

The control element 50 comprises a receiving module 60 designed to receive, here via a wireless link, setpoint information, i.e. information indicating the values desired by the user for the spherical power S, the cylindrical power C and the angle of astigmatism α that define the compensation generated by the optical system formed from the optical elements 2, 4, 6.

The receiving module 60 is for example an infrared receiving module that receives this setpoint information from an infrared emitting remote control controlled by the user. As a variant, provision could be made for this setpoint information to be received from a personal computer via a wireless link, for example a local wireless network; the user could in this case choose values of spherical power S, cylindrical power C and angle of astigmatism α for the visual compensation device by interactive selection on the computer.

The receiving module 60 transmits the setpoint information S, C, α received to a computing machine 66 (for example consisting of a processor executing a computer program so as to perform the functions of the computing machine, as described below), specifically to a converting module 68 implemented by this computing machine 66.

The converting module 68 determines the values of the angles $\alpha_1$, $\alpha_2$ and the value of the spherical power $S_V$ required to obtain the setpoint values S, C, α received as input, in accordance with what is described below with reference to FIG. 6.

The computing machine 66 also implements a control module 70 that receives as input the values of angles $\alpha_1$, $\alpha_2$ and spherical power $S_V$ computed by the converting module 68 and emits control signals to the motors 42, 44, 46, in order to control each of the motors 42, 44, 46 independently of the others so as to obtain respective positions for the toothed wheels 22, 24, 27 that allow the desired values to be obtained:

- the control module 70 controls the first motor 42 so as to make the first toothed wheel 22 turn about the optical axis X as far as the position in which the axis $Y_1$ of the optically active cylindrical surface of the convex planar-cylindrical lens 2 (borne by the first toothed wheel 22) makes an angle $\alpha_1$ with the reference direction $Y_0$;
- the control module 70 controls the second motor 44 so as to make the second toothed wheel 24 turn about the optical axis X as far as the position in which the axis $Y_2$ of the optically active cylindrical surface of the concave planar-cylindrical lens 4 (borne by the second toothed wheel 24) makes an angle $\alpha_2$ with the reference direction $Y_0$; and
- the control module 70 controls the third motor 46 so as to make the third toothed wheel 27 turn about the optical axis X as far as the position in which the ring for controlling the variable spherical power sets the spherical power $S_V$ to the power computed by the converting module 68.

The position of each toothed wheel 22, 24, 27 is known at each instant by virtue of the optical cells 52, 54, 56, respectively, which each measure, on the toothed wheel with which each is associated, the number of teeth that have passed through the optical cell relative to a reference point on the circumference of the wheel in question (for example a point devoid of teeth).

In the example described here, the first motor 42/first worm screw 32/first toothed wheel 22 assembly, just like the second motor 44/second worm screw 34/second toothed wheel 24 assembly, has a gear ratio such that one turn of the toothed wheel 22, 24 corresponds to 15040 micro-steps of the associated motor 42, 44. The resolution (angle of rotation of the toothed wheels 22, 24 for one micro-step) is therefore 0.024° for the angles $\alpha_1$ and $\alpha_2$.

The third motor 46/third worm screw 36/third toothed wheel 46 assembly for its part has a gear ratio of 16640 micro-steps per turn. The ring for controlling the variable spherical power is adjustable over an angular span of 120° (therefore corresponding to 5547 micro-steps) so as to obtain the variation in spherical power from −25 D to 25 D (i.e. a span of variation of 50 D). The resolution (variation in spherical power $S_V$ for one micro-step) is therefore 0.009 D.

According to one envisionable embodiment, provision may be made for the control element 50 to take into account the distance between the entrance face of the spherical lens 6 and the vertex of the cornea of an eye observing through the visual compensation device, in order optionally to correct the power setpoints of the visual compensation device in question. This distance (sometimes denoted LED for "lens-eye distance") may be obtained by known means for doing so.

Taking the example of a spherical power S of equivalent focal length F, a positioning error ε would mean a correction of focal length F' would be required, equivalent to a spherical power S', where:

$F'=F-\varepsilon$ and $$S' = S\left(\frac{1}{1 - \frac{\varepsilon}{F}}\right),$$

which to a first approximation gives S'=S·(1+ε·S).

The control element 50 therefore determines, according to this embodiment, the values of the angles $\alpha_1$, $\alpha_2$ and the value of spherical power $S_V$ (and the control signals to respectively be applied to the motors as indicated above) not only depending on the setpoint values S, C, α received as input but also depending on the eye-device (here the cornea-entrance face of the lens 6) distance. It will be noted that the lens-eye distance is here taken into account by the control element 50, which receives raw setpoints (i.e. without the lens-eye distance accounted for).

Moreover, provision may be made, during passage from initial setpoint values $\alpha_1$, $\alpha_2$, $S_V$ to new setpoint values $\alpha'_1$, $\alpha'_2$, $S'_V$, for each of the first, second and third motors 42, 44, 46 to be actuated for a given length of time T (in seconds) that may optionally depend on the amplitude of one of the setpoint changes (for example on the variation, in absolute value, in spherical power $|S'_V - S_V|$, where |x| is the absolute value of x).

To do this, the computing machine 66 for example determines the number $p_1$ of micro-steps of the motor 42 allowing passage from the angle $\alpha_1$ to the angle $\alpha'_1$, the number $p_2$ of micro-steps of the motor 44 allowing passage from the angle $\alpha_2$ to the angle $\alpha'_2$ and the number $p_3$ of micro-steps of the motor 46 allowing passage from the spherical power $S_V$ to the spherical power $S'_V$. The computing machine 66 then commands the motor 42 to rotate at a speed of $p_1/T$ micro-steps per second, the motor 44 to rotate at a speed of $p_2/T$ micro-steps per second and the motor 46 to rotate at a speed of $p_3/T$ micro-steps per second.

The control element 50 also comprises a temperature sensor 62, which delivers information on measured ambient temperature, and an inclinometer 64, for example taking the form of an accelerometer, which delivers information on the orientation of the visual compensation device 10, for example relative to the vertical.

The computing machine 66 receives the item of temperature information generated by the temperature sensor 62 and the item of orientation information generated by the inclinometer 64 and uses these items of information in the context of the determination of the commands to send to the motors 42, 44, 46.

In the example described, the control module 70 uses the item of temperature information in order to compensate for variations in the spherical power of the lens 6 due to temperature (about 0.06 D/° C. in the described example) and the item of orientation information in order to compensate for possible disturbances of the drive system (motors, worm screws, toothed wheels) due to changes in the orientation of the visual compensation device 10.

An example of a way in which the converting module 68 may be constructed will now be described with reference to FIG. 6.

As already indicated, this converting module 68 is designed to determine the values of the angles $\alpha_1$, $\alpha_2$ and the value of spherical power $S_V$ required to obtain the setpoint values S, C, α received as input, here using a model taking into account the distances $e_1$, $e_2$ separating the various lenses.

As already indicated for the computing machine 66, the converting module 68 is shown in FIG. 6 in the form of functional blocks, but could in practice be implemented via the execution, by a processor (for example a microprocessor), of computer program instructions.

The converting module 68 comprises a first block 80 that receives as input the setpoint values S, C, α and determines on this basis approximate values $\tilde{\alpha}_1, \tilde{\alpha}_2, \tilde{S}_V$ for the angles $\alpha_1$, $\alpha_2$ and the spherical power $S_V$, for example as follows:

$$\begin{cases} \tilde{\alpha}_1 = \alpha - \frac{1}{2}\arcsin\left(\frac{C}{2C_0}\right) + \frac{\pi}{4} \\ \tilde{\alpha}_2 = \alpha + \frac{1}{2}\arcsin\left(\frac{C}{2C_0}\right) + \frac{\pi}{4} \end{cases}$$

$$\tilde{S}_V = S + \frac{C}{2}$$

It will be noted that these formulae are based on those given above and do not take into account the spacings $e_1$, $e_2$ separating the various lenses (hence the obtained results are designated as "approximate values").

The approximate values $\tilde{\alpha}_1, \tilde{\alpha}_2, \tilde{S}_V$ are transmitted to a second block 82 and to an adder block 88.

The second block 82 receives as input the approximate values and estimates the values of spherical power S', cylindrical power C' and angle of astigmatism α' that would be obtained (with the optical system formed from the two cylindrical lenses 2, 4 and the lens 6 of variable spherical power) if the approximate values $\tilde{\alpha}_1, \tilde{\alpha}_2, \tilde{S}_V$ received were used in the device. This estimation is based on a model taking into account the distances $e_1$, $e_2$ separating the various lenses.

Here for example, using Gullstrand's equations, the optical power for each meridian (indicated by an angle ϕ) is (with the optical system formed from the two cylindrical lenses 2, 4 and the lens 6 of variable spherical power):

$$P(\phi)=S_V+A_1(S_V)\cdot P_1(\phi)+A_2(S_V)\cdot P_2(\phi)+A_3(S_V)\cdot P_1(\phi)\cdot P_2(\phi)$$

where $$P_1(\phi)=C_1\sin^2(\tilde{\alpha}_1-\phi)$$

$$P_2(\phi)=C_2\sin^2(\tilde{\alpha}_2-\phi)$$

$$A_1(S_V)=1+(e_1-e_2-K)\cdot S_V$$

$$A_2(S_V)=1-(e_2+K)\cdot S_V$$

$$A_3(S_V)=-e_1\cdot(1-(K(S_V)+e_2)\cdot S_V)$$

$$K = w_0 - h\cdot\left(1 - \frac{1}{n_{LV}}\right),$$

where $w_0$ is the bow of the lens 6, h the thickness of the lens 6 and $n_{LV}$ the index of the liquid filling the lens 6, K being the distance between the rest position of the membrane and the principal object plane of the variable lens.

The parameters A1, A2 and A3 are therefore variable functions of $S_V$, whereas the other parameters are constants of the system (which may be calibrated).

By definition of the spherical power, of the cylindrical power and of the angle of astigmatism of the optical system, this optical power P may also be written, for each meridian:

$$P(\phi)=S'+C'\sin^2(\alpha'-\phi).$$

It is thus for example possible to obtain C' and a' by calculating the derivative dP/dϕ of the function P(ϕ) and by taking 2 particular values (for example ϕ=0 and ϕ=π/4), this allowing tan 2α' and $C'^2$ to be obtained.

The constant portion of P(ϕ) moreover gives access to S' according to the above equation.

The values of spherical power S', of cylindrical power C' and of angle of astigmatism α' generated as output from the second block 82 are transmitted to a subtracter block 84, which computes the difference between each of these values and the corresponding setpoint value S, C, α. The subtracter block 84 thus outputs the following values (which represent, for each parameter, the error due to the use of the approximate values):

$$\Delta S=S-S'; \Delta C=C-C'; \Delta\alpha=\alpha-\alpha'.$$

The error values ΔS, ΔC, Δα output from the subtracter block 84 are input into a third block 86 that is designed to determine the respective variations $\Delta\alpha_1, \Delta\alpha_2, \Delta S_V$ in the settings $\alpha_1, \alpha_2, S_V$ associated with these error values ΔS, ΔC, Δα (for example by linearization of the equality:

$$S'+C'\sin^2(\alpha'-\phi)=S_V+A_1(S_V)\cdot P_1(\phi)+A_2(S_V)\cdot P_2(\phi)+A_3(S_V)\cdot P_1(\phi)\cdot P_2(\phi)$$

around the values S', C', α' and $\tilde{\alpha}_1, \tilde{\alpha}_2, \tilde{S}_V$). The values of ΔS are for example obtained for $\tilde{\alpha}_1, \tilde{\alpha}_2$ and $\tilde{S}_V$ by respectively taking the derivatives $dS'/d(\tilde{\alpha}_1)$, $dS'/d(\tilde{\alpha}_2)$, and $dS'/d(\tilde{S}_V)$. The process is identical for ΔC and Δα. Next, the obtained system of equations is solved conventionally using particular values.

The setting variations $\Delta\alpha_1, \Delta\alpha_2, \Delta S_V$ are then input into the adder block 88 that also receives as input, as already indicated, the approximate values $\tilde{\alpha}_1, \tilde{\alpha}_2, \tilde{S}_V$ generated by the first block 80.

This adder block 88 therefore generates as output the following setting values:

$$\alpha_1=\tilde{\alpha}_1+\Delta\alpha_1;$$

$$\alpha_2=\tilde{\alpha}_2+\Delta\alpha_2;$$

$$\Delta S_V=\tilde{S}_V+\Delta S_V.$$

By virtue of the calculations performed above, these setting values $\alpha_1, \alpha_2, S_V$ allow the setpoint values S, C, α to be obtained while taking into account coupling effects related to the spacing of the lenses, with a minimum error related to the approximation made during the linearization used within the third block 86.

According to one envisionable variant, as shown by the dashed line in FIG. 6, it is possible to apply one or more new iterations of the process described above in order to make each of the error values ΔS, ΔC, Δα converge toward 0 (the iterative process for example stopping when each of the error values is lower than a preset threshold). For these subsequent iterations, the setting values $\alpha_1, \alpha_2, S_V$ output from the preceding iteration are used by way of approximate values $\tilde{\alpha}_1, \tilde{\alpha}_2, \tilde{S}_V$ in the current iteration.

It will be understood that the process that has just been described allows, depending on setpoint values S, C, α, setting values $\alpha_1, \alpha_2, S_V$ to be determined in real-time by means of a model taking into account the distances $e_1$, $e_2$ separating the various lenses 2, 4, 6.

According to another envisionable embodiment, the converting module 68 could store in memory (within a look up table or LUT) many triplets $(\alpha_1, \alpha_2, S_V)$ of setting values and, for each triplet $(\alpha_1, \alpha_2, S_V)$, the triplet of values (S, C, α) obtained using the setting values $\alpha_1, \alpha_2, S_V$ in question.

The triplets of values (S, C, α) associated with a triplet of setting values $(\alpha_1, \alpha_2, S_V)$ are computed beforehand using a module taking into account the distances separating the lenses 2, 4, 6 (for example by means of the equations given above) and stored in memory, as already indicated, in the converting module 68.

In practice, triplets associated with possible values of S and C that are regularly distributed over the envisionable value ranges are stored in memory. For example, 160 values of S in the range [−20 D, 20 D] (this corresponding to an interval of 0.25 D) and 32 values of C in the range [0, 8 D] (this also corresponding to an interval of 0.25 D) are used and the parameter α is processed by simple rotation, this allowing only 5120 triplets of setting values ($\alpha_1$, $\alpha_2$, $S_V$), each associated with one pair (S, C), to be stored in memory.

In operation, the converting module 68 selects, from the stored triplets (S, C, α), the triplet the values of which are closest to the setpoint values S, C, α received as input; the converting module 68 then reads the triplet of setting values ($\alpha_1$, $\alpha_2$, $S_V$) that is associated (in the look up table) with the selected triplet and outputs the values read.

In the practical example that was just mentioned, the triplets ($\alpha_1$, $\alpha_2$, $S_V$) are stored in memory each in association with a pair (S, C), and the converting module 68 reads the values ($\alpha_1$, $\alpha_2$, $S_V$) associated with the pair the values of which are closest to the setpoint values S, C and makes a rotational correction in order to take into account the angle α.

According to one envisionable variant, it is possible to furthermore take into account temperature (in order to compensate, as indicated above, for variations in the spherical power of the lens 6 due to temperature). The converting module 68 for example in this case stores in memory a plurality of look up tables each associated with one given temperature. In use, the converting module 68 selects the look up table associated with the item of temperature information delivered by the temperature sensor 62 and performs the processing described above using the selected look up table.

According to another envisionable embodiment, the converting module 68 could determine the values of the angles $\alpha_1$, $\alpha_2$ and the value of the spherical power $S_V$ required to obtain the setpoint values S, C, α received as input by means of a ray-tracing simulation, the ray tracing being carried out in an environment in which the lenses 2, 4, 6 are modelled in their respective positions and that therefore takes into account the distances separating these lenses 2, 4, 6.

The visual compensation device 10 may be used to provide the Jackson-cross-cylinder function, Jackson cross-cylinders also being referred to as flip cross cylinders.

According to a first example, this function may be used to verify (or even find) an angle $\alpha_0$ of required cylindrical correction (parameter sometimes denoted "cylinder axis"). Here, it is assumed that a spherical power correction value $S_0$ and a cylindrical power correction value $C_0$ have also been determined beforehand.

The Jackson-cross-cylinder function is then for example provided by applying in rapid alternation two sets of setpoints, namely a first set of setpoints corresponding to an addition of cylindrical power $C_{var}$ (for example 0.5 D) at 45° from the axis defined by the angle $\alpha_0$:

an angle of astigmatism setpoint $\alpha_1 = \alpha_0 - 0.5 \cdot a\, \tan(C_{var}/C_0)$;
a cylindrical power setpoint $C_1 = \text{Root}(C_0^2 + C_{var}^2)$, where Root is the square root function; and
a spherical power setpoint $S_1 = S_0 + C_0/2 - C_1/2$,
and a second set of setpoints corresponding to an addition of cylindrical power $-C_{var}$ at 45° from the axis defined by the angle $\alpha_0$:

an angle of astigmatism setpoint $\alpha_2 = \alpha_0 - 0.5 \cdot a\, \tan(C_{var}/C_0)$;
a cylindrical power setpoint $C_2 = \text{Root}(C_0^2 + C_{var}^2)$; and
a spherical power setpoint $S_2 = S_0 + C_0/2 - C_2/2$, According to a second example, this function may be used to verify (or even find) the value of the required cylindrical power correction value $C_0$. Here, it is assumed that a spherical power correction value $S_0$ and an angle of astigmatism value $\alpha_0$ have also been determined beforehand.

The Jackson-cross-cylinder function is then for example provided by applying in rapid alternation two sets of setpoints, namely a first set of setpoints corresponding to an addition of cylindrical power $C_{var}$ (for example 0.5 D) on the axis defined by the angle $\alpha_0$:

an angle of astigmatism setpoint $\alpha_1 = \alpha_0$;
a cylindrical power setpoint $C_1 = C_0 + C_{var}$; and
a spherical power setpoint $S_1 = S_0 - C_{var}/2$, and a second set of setpoints corresponding to an addition of cylindrical power $-C_{var}$ on the axis defined by the angle $\alpha_0$:

an angle of astigmatism setpoint $\alpha_2 = \alpha_0$;
a cylindrical power setpoint $C_2 = C_0 - C_{var}$; and
a spherical power setpoint $S_2 = S_0 + C_{var}/2$.

The invention claimed is:

1. A visual compensation device allowing observation along an optical axis of observation with an optical correction of variable power, the visual compensation device comprising:
a lens having, along the optical axis, a variable spherical power that depends on a first setting;
an optical assembly generating, along the optical axis, a variable cylindrical correction that depends on at least one second setting applied to said optical assembly;
a module for receiving at least one setpoint for said optical correction; and
a module for determining the first setting and the second setting depending on said setpoint by a model taking into account the distance separating said lens and said optical assembly.

2. The visual compensation device as claimed in claim 1, wherein the module for determining the first setting and the second setting comprises:
a module for determining an approximate first setting value and an approximate second setting value depending on said setpoint;
a module for evaluating, on the basis of said model, at least one correction value obtained by applying the approximate first setting value to the lens and the approximate second setting value to the optical assembly;
a module for determining a first corrected setting value and a second corrected setting value on the basis of a comparison between the setpoint and the evaluated correction value.

3. The visual compensation device as claimed in claim 2, wherein the module for determining the first setting and the second setting is designed to use the first corrected setting value and the second corrected setting value respectively by the first setting and the second setting.

4. The visual compensation device as claimed in claim 1, wherein the module for determining the first setting and the second setting is designed to read the first setting from a look up table constructed on the basis of said model.

5. The visual compensation device as claimed in claim 1, wherein the optical assembly comprises a second lens and a third lens, and wherein the model takes into account the distance separating the second lens and the third lens.

6. An optometric binocular device comprising:
two optical devices,
wherein at least one of the two optical devices is the visual compensation device according to claim 1.

7. A method for controlling a visual compensation device allowing observation along an optical axis of observation with an optical correction of variable power and comprising a lens and an optical assembly, said method comprising:
receiving at least one setpoint for said optical correction;
determining a first setting and a second setting depending on said setpoint by a model taking into account the distance separating said lens and said optical assembly;
modifying the spherical power of the lens along the optical axis depending on the first setting; and
modifying a cylindrical correction generated along the optical axis by the optical assembly depending on the second setting.

8. The control method as claimed in claim 7, wherein the step of determining a first setting and a second setting comprises:
determining an approximate first setting value and an approximate second setting value depending on said setpoint,
evaluating, on the basis of said model, at least one correction value obtained by applying the approximate first setting value to the lens and the approximate second setting value to the optical assembly, and
determining a corrected first setting value and a corrected second setting value on the basis of a comparison between the setpoint and the evaluated correction value.

9. The control method as claimed in claim 8, further comprising:
evaluating, on the basis of said model, at least one new correction value obtained by applying the corrected first setting value to the lens and the corrected second setting value to the optical assembly; and
determining a new corrected first setting value and a new corrected second setting value on the basis of a comparison between the setpoint and the evaluated new correction value.

10. The control method as claimed in claim 9, wherein the evaluating at least one new correction value and the determining a new corrected first setting value and a new corrected second setting value are reiterated provided that the distance between the setpoint and the evaluated new correction value is larger than a preset threshold.

11. The control method as claimed in claim 7, wherein the determining a first setting and a second setting comprises reading the first setting from a look-up table constructed on the basis of said model.

12. The control method as claimed in claim 7, wherein the optical assembly comprises a second lens and a third lens, and
wherein the model takes into account the distance separating the second lens and the third lens.

* * * * *